(12) United States Patent
Kulkarni (10) Patent No.: US 10,782,307 B1
(45) Date of Patent: Sep. 22, 2020

(54) USE OF REMNANT LIPOPROTEIN IN THE TREATMENT AND PREVENTION OF CARDIOVASCULAR DISEASE

(71) Applicant: The UAB Research Foundation, Birmingham, AL (US)

(72) Inventor: Krishnaji R. Kulkarni, Vestavia, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 14/639,388

(22) Filed: Mar. 5, 2015

Related U.S. Application Data

(60) Provisional application No. 61/948,410, filed on Mar. 5, 2014.

(51) Int. Cl.
| | |
|---|---|
| *G01N 33/50* | (2006.01) |
| *G01N 33/92* | (2006.01) |
| *A61P 9/10* | (2006.01) |
| *A61P 3/06* | (2006.01) |
| *C07K 14/775* | (2006.01) |

(52) U.S. Cl.
CPC ............... *G01N 33/92* (2013.01); *A61P 3/06* (2018.01); *A61P 9/10* (2018.01); *G01N 33/50* (2013.01); *C07K 14/775* (2013.01); *G01N 2405/00* (2013.01); *G01N 2800/044* (2013.01); *G01N 2800/32* (2013.01); *G01N 2800/323* (2013.01); *G01N 2800/324* (2013.01); *G01N 2800/50* (2013.01)

(58) Field of Classification Search
None
See application file for complete search history.

(56) References Cited

PUBLICATIONS

Lipoprotein Subfractionation Profile, 2008. A Technical Review published by LabCorp, available at www.labcorp.com/.EdosPortlet/TestMenuLibrary?libName=File+Library&compName=L1052. 8 pages as printed. No author indicated, no month of publication available.*
Kulkarni et al (1994. J. Lipid Res. 35: 159-168).*
Chung et al (1986. Methods in Enzymology. 128: 181-209).*
May et al (2013. Lipids in Health and Disease. 12(55): 1-13; published Apr. 2013.*

* cited by examiner

*Primary Examiner* — Zachary C Howard
(74) *Attorney, Agent, or Firm* — Thomas G. Peterson; Maynard Cooper & Gale (57) ABSTRACT

The present disclosure provides a variety of methods based on the determination of cholesterol concentration in remnant lipoprotein and/or the determination of a remnant lipoprotein level in a sample from a subject. Such methods include, but are not limited to, a method of predicting the risk of cardiovascular disease, a method for evaluating a subject for treatment for a cardiovascular disease and a method for determining if a subject is suffering from cardiovascular disease.

16 Claims, 4 Drawing Sheets

USE OF REMNANT LIPOPROTEIN IN THE TREATMENT AND PREVENTION OF CARDIOVASCULAR DISEASE

FIELD OF THE DISCLOSURE

The present application provides method for predicting the risk of cardiovascular disease in a subject. More specifically the present disclosure relates to methods of predicting the risk of cardiovascular disease in a subject by determining remnant lipoprotein levels or remnant lipoprotein cholesterol levels in the subject.

BACKGROUND

The measurement of blood lipoproteins is critical in predicting an individual's risk of many chronic diseases, particularly cardiovascular disease such as coronary heart disease (CHD)/coronary artery disease (CAD). CHD/CAD continues to be the leading cause of death in the United States despite phenomenal advances made in its diagnosis, treatment, and prevention in the last 3 decades. As per the recently released Heart and Stroke Statistics (2014 Update by the American Heart Association; *Circulation* 2014; 129: e28-e292), this disease accounts for 1 in 6 deaths in the US. In 2010 as many as 379,559 people died of CHD/CAD and ~620,000 were expected to have a new heart attack and another 295,000 people with recurrent attacks. These astounding statistics clearly tell us that prevention of heart disease still remains a formidable task.

Consequently, there is a long-felt but unmet need in the art to develop newer, simpler, and more accurate methods for the determination/prediction of the risk of cardiovascular disease. The present disclosure provides methods for predicting the risk of cardiovascular disease in a subject, methods for evaluating a subject for treatment for a cardiovascular disease and method for determining if a subject is suffering from a cardiovascular disease. Such methods were heretofore not appreciated in the art.

SUMMARY OF THE DISCLOSURE

In a first aspect, the present disclosure provides methods for predicting the risk of cardiovascular disease in a sample from the subject.

In a second aspect, the present disclosure provides methods for predicting the risk of cardiovascular disease in a subject by determining a remnant lipoprotein level in the subject.

In a third aspect, the present disclosure provides methods for predicting the risk of cardiovascular disease in a subject by determining the cholesterol concentration in a remnant lipoprotein in a sample from the subject.

In a fourth aspect, the present disclosure provides methods for predicting the risk of cardiovascular disease in a subject by determining a remnant lipoprotein level in the subject, wherein the remnant lipoprotein level comprises, consists of or consists essentially of the level of IDL and one or more subsets of VLDL lipoprotein in a sample from the subject.

In a fifth aspect, the present disclosure provides methods for predicting the risk of cardiovascular disease in a subject by determining a cholesterol concentration in a remnant lipoprotein in the subject, wherein the remnant lipoprotein comprises, consists of or consists essentially of IDL and one or more subsets of VLDL lipoprotein in a sample from the subject.

In a sixth aspect, the present disclosure provides methods for predicting the risk of cardiovascular disease in a subject by determining a remnant lipoprotein level in the subject, wherein the remnant lipoprotein level comprises, consists of or consists essentially of the level of IDL and VLDL3 lipoprotein in a sample from the subject.

In a seventh aspect, the present disclosure provides methods for predicting the risk of cardiovascular disease in a subject by determining a cholesterol concentration in a remnant lipoprotein in the subject, wherein the remnant lipoprotein comprises, consists of or consists essentially of IDL and VLDL3 lipoprotein in a sample from the subject.

In an eighth aspect, the present disclosure provides methods for predicting the risk of cardiovascular disease in a subject by determining a remnant lipoprotein level in the subject, wherein the remnant lipoprotein level comprises, consists of or consists essentially of IDL lipoprotein in a sample from the subject.

In a ninth aspect, the present disclosure provides methods for predicting the risk of cardiovascular disease in a subject by determining a cholesterol concentration in a remnant lipoprotein in the subject, wherein the remnant lipoprotein comprises, consists of or consists essentially of the IDL lipoprotein in a sample from the subject.

In tenth aspect, the present disclosure provides methods for predicting the risk of cardiovascular disease in a subject by determining a remnant lipoprotein level in the subject, wherein the remnant lipoprotein level consists of or consists essentially of IDL lipoprotein in a sample from the subject or consists of or consists essentially of VLDL3 lipoprotein in a sample from the subject.

In an eleventh aspect, the present disclosure provides methods for predicting the risk of cardiovascular disease in a subject by determining a cholesterol concentration in a remnant lipoprotein in the subject, wherein the remnant lipoprotein consists of or consists essentially of the IDL lipoprotein in a sample from the subject or consists of or consists essentially of VLDL3 lipoprotein in a sample from the subject.

In a further embodiment of the first through eleventh aspects, an increase in level of remnant lipoproteins indicates the subject is at increased risk for cardiovascular disease. Such an increase in level of remnant lipoproteins may be determined with respect to the levels of IDL and one or more classes of VLDL, with respect to the levels of IDL plus VLDL3, with respect to the levels of IDL alone or with respect to the levels of VLDL3 alone. In one embodiment, the foregoing is determined with respect to the levels of IDL and VLDL3 lipoprotein. In another embodiment, the increased risk is determined with respect to the levels of IDL lipoprotein alone. In another embodiment, the increased risk is determined with respect to the levels of VLDL3 lipoprotein alone.

In a further embodiment of the first through eleventh aspects, an increase in cholesterol concentration as measured in the remnant lipoprotein indicates the subject is at increased risk for cardiovascular disease. Such an increase cholesterol concentration as measured in the remnant lipoprotein may be determined with respect to the levels of IDL and one or more classes of VLDL3, with respect to the levels of IDL and VLDL3, with respect to IDL alone or with respect to VLDL3 alone. In one embodiment, the increased risk is determined with respect to the levels of IDL and VLDL3. In another embodiment, the increased risk is determined with respect to the cholesterol concentration as measured in IDL lipoprotein. In another embodiment, the increased risk is determined with respect to the levels of VLDL3 lipoprotein alone.

In a twelfth aspect, the present disclosure provides a method for evaluating a subject for treatment for a cardiovascular disease by determining a remnant lipoprotein level in a sample from the subject.

In a thirteenth aspect, the present disclosure provides a method for evaluating a subject for treatment for a cardiovascular disease by determining a cholesterol concentration in a remnant lipoprotein in a sample from the subject.

In a fourteenth aspect, the present disclosure provides a method for evaluating a subject for treatment for a cardiovascular disease by determining a remnant lipoprotein level in the subject, wherein the remnant lipoprotein level comprises, consists of or consists essentially of the level of IDL and one or more subsets of VLDL lipoprotein in a sample from the subject.

In a fifteenth aspect, the present disclosure provides a method for evaluating a subject for treatment for a cardiovascular disease by determining a cholesterol concentration in a remnant lipoprotein in the subject, wherein the remnant lipoprotein comprises, consists of or consists essentially of IDL and one or more subsets of VLDL lipoprotein in a sample from the subject.

In a sixteenth aspect, the present disclosure provides a method for evaluating a subject for treatment for a cardiovascular disease by determining a remnant lipoprotein level in the subject, wherein the remnant lipoprotein level comprises, consists of or consists essentially of the level of IDL and VLDL3 lipoprotein in a sample from the subject.

In a seventeenth aspect, the present disclosure provides a method for evaluating a subject for treatment for a cardiovascular disease by determining a cholesterol concentration in a remnant lipoprotein in the subject, wherein the remnant lipoprotein comprises, consists of or consists essentially of IDL and VLDL3 lipoprotein in a sample from the subject.

In an eighteenth aspect, the present disclosure provides a method for evaluating a subject for treatment for a cardiovascular disease by determining a remnant lipoprotein level in the subject, wherein the remnant lipoprotein level comprises, consists of or consists essentially of IDL lipoprotein in a sample from the subject.

In a nineteenth aspect, the present disclosure provides a method for evaluating a subject for treatment for a cardiovascular disease by determining a cholesterol concentration in a remnant lipoprotein in the subject, wherein the remnant lipoprotein comprises, consists of or consists essentially of IDL lipoprotein in a sample from the subject.

In twentieth aspect, the present disclosure provides a method for evaluating a subject for treatment for a cardiovascular disease by determining a remnant lipoprotein level in the subject, wherein the remnant lipoprotein level consists of or consists essentially of IDL lipoprotein in a sample from the subject or consists of or consists essentially of VLDL3 lipoprotein in a sample from the subject.

In a twenty-first aspect, the present disclosure provides a method for evaluating a subject for treatment for a cardiovascular disease by determining a cholesterol concentration in a remnant lipoprotein in the subject, wherein the remnant lipoprotein consists of or consists essentially of VLDL3 lipoprotein in a sample from the subject.

In a further embodiment of the twelfth through twenty-first, when the evaluation indicates an increase in the remnant lipoproteins level, the subject is at an increased risk for cardiovascular disease. As a result, a healthcare provider makes a decision regarding care of the subject. Such a decision may involve a decision to initiate treatment for a cardiovascular disease, a decision to initiate or increase monitoring of the subject for a cardiovascular disease, a decision to initiate preventive measures in the subject and/or a decision to initiate lifestyle changes in the subject to reduce the risk of cardiovascular disease. Such an increase in level of remnant lipoproteins may be determined with respect to the levels of IDL and one or more classes of VLDL, with respect to the levels of IDL and VLDL3, with respect to the levels of IDL alone or with respect to the levels of VLDL3 alone. In one embodiment, the foregoing is determined with respect to the levels of IDL and VLDL3. In another embodiment, the increased risk is determined with respect to the levels of IDL lipoprotein alone. In another embodiment, the increased risk is determined with respect to the levels of VLDL3 lipoprotein alone.

In one embodiment of the twelfth through twenty-first aspects, the method for evaluating a subject for treatment for a cardiovascular disease involves determining if the remnant lipoprotein level is increased and initiating treatment in the subject for a cardiovascular disease if such level is increased.

In another embodiment of the twelfth through twenty-first aspects, the method for evaluating a subject for treatment for a cardiovascular disease involves determining if the remnant lipoprotein level is increased and initiating or increasing monitoring of the health of the subject, particularly monitoring the health of the subject with respect to cardiovascular disease, when such level is increased.

In a further embodiment of the twelfth through twenty-first aspects, the method for evaluating a subject for treatment for a cardiovascular disease involves determining if the remnant lipoprotein level is increased and initiating preventive measures in the subject if such level is increased.

In a further embodiment of the twelfth through twenty-first aspects, the method for evaluating a subject for treatment for a cardiovascular disease involves determining if the remnant lipoprotein level is increased and initiating lifestyle changes in the subject to reduce the risk of cardiovascular disease if such level is increased.

In a further embodiment of the twelfth through twenty-first, when the evaluation indicates an increase in cholesterol concentration as measured in the remnant lipoprotein the subject is at an increased risk for cardiovascular disease. As a result, a healthcare provider makes a decision regarding care of the subject. Such a decision may involve a decision to initiate treatment for a cardiovascular disease, a decision to initiate or increase monitoring of the subject for a cardiovascular disease, a decision to initiate preventive measures in the subject and/or a decision to initiate lifestyle changes in the subject to reduce the risk of cardiovascular disease. Such an increase cholesterol concentration as measured in the remnant lipoprotein levels may be determined with respect to the levels of IDL and one or more subclasses of VLDL, with respect to the levels of IDL and VLDL3, with respect to IDL alone or with respect to VLDL3 alone. In one embodiment, the increased risk is determined with respect to the levels of IDL and VLDL3. In another embodiment, the increased risk is determined with respect to the cholesterol concentration as measured in IDL lipoprotein. In another embodiment, the increased risk is determined with respect to the cholesterol concentration as measured in VLDL3 lipoprotein.

In one embodiment of the twelfth through twenty-first aspects, the method for evaluating a subject for treatment for a cardiovascular disease involves determining if the cholesterol concentration in the remnant lipoprotein is increased and initiating treatment in the subject for a cardiovascular disease if such concentration is increased.

In another embodiment of the twelfth through twenty-first aspects, the method for evaluating a subject for treatment for a cardiovascular disease involves determining if the cholesterol concentration in the remnant lipoprotein is increased and initiating or increasing monitoring of the health of the subject, particularly monitoring the health of the subject with respect to cardiovascular disease, is such concentration is increased.

In a further embodiment of the twelfth through twenty-first aspects, the method for evaluating a subject for treatment for a cardiovascular disease involves determining if the cholesterol concentration in the remnant lipoprotein is increased and initiating preventive measures in the subject if such concentration is increased.

In a further embodiment of the twelfth through twenty-first aspects, the method for evaluating a subject for treatment for a cardiovascular disease involves determining if the cholesterol concentration in the remnant lipoprotein is increased and initiating lifestyle changes in the subject to reduce the risk of cardiovascular disease if such concentration is increased.

In a twenty-second aspect, the present disclosure provides a method for determining if a subject is suffering from a cardiovascular disease, the method comprising determining a remnant lipoprotein level in a sample from the subject.

In a twenty-third aspect, the present disclosure provides a method for determining if a subject is suffering from a cardiovascular disease, the method comprising determining the cholesterol level in a remnant lipoprotein in a sample from the subject.

In a twenty-fourth aspect, the present disclosure provides a method for determining if a subject is suffering from a cardiovascular disease, the method comprising determining a remnant lipoprotein level in the subject, wherein the remnant lipoprotein level comprises, consists of or consists essentially of IDL and one or more subsets of VLDL lipoprotein in the subject.

In a twenty-fifth aspect, the present disclosure provides a method for determining if a subject is suffering from a cardiovascular disease, the method comprising obtaining a cholesterol concentration in the remnant lipoprotein of the subject, wherein the remnant lipoprotein comprises, consists of or consist essentially of the level of IDL and one or more subsets of VLDL lipoprotein in a sample from the subject.

In a twenty-sixth aspect, the present disclosure provides a method for determining if a subject is suffering from a cardiovascular disease, the method comprising determining a remnant lipoprotein level in the subject, wherein the remnant lipoprotein level comprises, consists of or consists essentially of IDL and VLDL3 lipoprotein in a sample from the subject.

In a twenty-seventh aspect, the present disclosure provides a method for determining if a subject is suffering from a cardiovascular disease, the method comprising obtaining a cholesterol concentration in the remnant lipoprotein of the subject, wherein the remnant lipoprotein comprises, consists of or consist essentially of IDL and VLDL3 lipoprotein in a sample from the subject.

In a twenty-eight aspect, the present disclosure provides a method for determining if a subject is suffering from a cardiovascular disease, the method comprising determining a remnant lipoprotein level in the subject, wherein the remnant lipoprotein level comprises, consists of or consists essentially of IDL lipoprotein in a sample from the subject.

In a twenty-ninth aspect, the present disclosure provides a method for determining if a subject is suffering from a cardiovascular disease, the method comprising obtaining a cholesterol concentration in the remnant lipoprotein of the subject, wherein the remnant lipoprotein comprises, consists of or consists essentially of IDL lipoprotein in a sample from the subject.

In thirtieth aspect, the present disclosure provides methods a method for determining if a subject is suffering from a cardiovascular disease, the method comprising determining a remnant lipoprotein level in the subject, wherein the remnant lipoprotein level consists of or consists essentially of IDL lipoprotein in a sample from the subject or consists of or consists essentially of VLDL3 lipoprotein in a sample from the subject.

In a thirty-first aspect, the present disclosure provides methods a method for determining if a subject is suffering from a cardiovascular disease, the method comprising determining a cholesterol concentration in the remnant lipoprotein of the subject, wherein the remnant lipoprotein consists of or consists essentially of IDL lipoprotein in a sample from the subject or consists of or consists essentially of VLDL3 lipoprotein in a sample from the subject.

In a further embodiment of the twenty-second through thirty-first aspects, an increase in level of remnant lipoproteins indicates the subject is suffering cardiovascular disease. Such an increase in level of remnant lipoproteins may be determined with respect to the levels of IDL and one or more subclasses of VLDL, with respect to the levels of IDL and VLDL3, with respect to the levels of IDL alone or with respect to the levels of VLDL3 alone. In one embodiment, the foregoing is determined with respect to the levels of IDL and VLDL3. In another embodiment, the foregoing is determined with respect to the levels of IDL lipoprotein alone. In another embodiment, the foregoing is determined with respect to the levels of VLDL3 lipoprotein alone.

In a further embodiment of the twenty-second through thirty-first aspects, an increase in cholesterol concentration as measured in the remnant lipoprotein indicates the subject is at suffering from cardiovascular disease. Such an increase cholesterol concentration as measured in the remnant lipoprotein may be determined with respect to the levels of IDL and one or more subclasses of VLDL3, with respect to the levels of IDL and VLDL3, with respect to IDL alone or with respect to VLDL3 alone. In one embodiment, the increased risk is determined with respect to the cholesterol concentration as measured IDL and VLDL3. In another embodiment, the foregoing is determined with respect to the cholesterol concentration as measured in IDL lipoprotein alone.

In another embodiment, the foregoing is determined with respect to the cholesterol concentration as measured in VLDL3 lipoprotein alone.

DETAILED DESCRIPTION

Definitions

With reference to the use of the word(s) "comprise" or "comprises" or "comprising" in the foregoing description and/or in the following claims, unless the context requires otherwise, those words are used on the basis and clear understanding that they are to be interpreted inclusively, rather than exclusively, and that each of those words is to be so interpreted in construing the foregoing description and/or the following claims.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "about" as used herein refers to a value that is within a range around a central value, the range being a margin of error that would be expected by one of ordinary skill in the art based on accepted methods of measurement of the particular central value.

The terms "approximate" and "approximately" as used herein refer to a difference between an actual relationship between two variables and a calculated regression between the two variables that is relatively minor. For example, such a relationship with a variance above 0.5 or below −0.5 could be said to approximate the calculated regression.

The term "total remnant lipoprotein" as used herein refers to IDL lipoprotein and VLDL lipoprotein or one or more subclass of VLDL lipoprotein, such as VLDL3, as specified. For example, in a preferred embodiment, "total remnant lipoprotein" is IDL lipoprotein and VLDL3 lipoprotein.

The term "IDL remnant lipoprotein" as used herein refers to IDL lipoprotein

The term "VLDL remnant lipoprotein" as used herein refers to VLDL lipoprotein or a specific subclass of VLDL lipoprotein, such as VLDL3, as specified.

As used herein, the terms "cardiovascular disease" or "cardiovascular disorder" are terms used to encompass a number of conditions affecting the heart as well as portions of the heart and systems related to the functioning of the heart, such as but not limited to, heart valves, and vasculature (e.g., arteries and veins) of the body. Such conditions, include, but are not limited to, arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease, peripheral artery disease, hypertriglyceridemia, and cerebrovascular disease.

As used herein, the term "atherosclerotic disease" refers to a subset of cardiovascular disease that involves atherosclerosis as a component or precursor. Such conditions include, but are not limited to, coronary artery disease, peripheral artery disease, and cerebrovascular disease. The term "atherosclerotic disease" also includes those conditions that result from plaque formation and rupture including, but not limited to, stenosis or narrowing of arteries, heart failure, aneurysm formation including aortic aneurysm, aortic dissection, and ischemic events such as myocardial infarction and stroke.

INTRODUCTION

Cardiovascular disease is a multi-factorial disease and several risk factors such as high blood pressure, smoking, elevated serum low density lipoprotein (LDL) cholesterol, and diabetes are attributed to an increased risk. Among these risk factors, LDL is known to be directly responsible for the build-up of the plaque within the arterial wall which results in subsequent coronary events. This is further supported by the fact that lowering LDL cholesterol by pharmacological means or lifestyle changes significantly reduces coronary events. However, only 50% of coronary events can be accounted by elevated LDL cholesterol and many studies suggest that coronary events can also occur even in people with normal LDL cholesterol. Therefore, in recent years there has been a surge in research in identifying new risk factors and biomarkers that may explain the risk of cardiovascular disease that cannot not be accounted by traditional risk factors.

Clinical evidence suggests that triglyceride-rich lipoproteins (TGRLP) play a significant role in the pathogenesis of cardiovascular disease. However, despite increased interest in the field, epidemiological studies have not identified plasma triglyceride concentration as an independent risk factor for cardiovascular disease. Despite a strong univariate association between plasma triglyceride levels and risk of cardiovascular disease, the relationship often fails to reach statistical significance when other traditional lipid risk factors are considered. One potential reason for this anomaly may be the heterogeneous nature of TGRLPs. Plasma triglyceride is carried in a number of different lipoproteins (eg, chylomicrons, large and small VLDL, and chylomicron and VLDL remnants), and the ability of different triglyceride-rich lipoproteins to promote cardiovascular disease is not the same.

Differences in the potential atherogenicity associated with different types of TGRLP particles can be illustrated by the prevalence of premature coronary artery disease (CAD) in patients with different inherited forms of hypertriglyceridemia. Type I or type V hyperlipoproteinemic patients have high triglyceride levels caused by lipoprotein lipase or apolipoprotein (apo)C-II deficiency. As a result, these patients have a significant increase in circulating levels of very large TGRLP. However, the patients are not at greatly increased risk of CAD and other diseases. This is in stark contrast to patients with type III hyperlipoproteinemia. Type III hyperlipoproteinemia is caused by reduced hepatic uptake of TGRLP remnants resulting in subsequent accumulation of the TGRLP remnants in plasma. While these patients have moderate hypertriglyceridemia, the patients do have an increased risk of CAD and peripheral vascular disease. TGRLP remnants, or simply remnants, are smaller, partially catabolized TGRLP. As exemplified above and by other studies, the remnants are believed to be more atherogenic or thrombogenic than larger, newly-secreted TGRLP. This atherogenic role of remnants is supported by experimental evidence showing that the smaller remnant particles can diffuse into the arterial intima and other areas where the larger TGRLP, such as chylomicrons and VLDL (diameter 75 nm or greater) are excluded as well as the fact that due to their reduced size, increased apoE content and association with lipoprotein lipase, remnants are more likely to be retained by heparan sulfate proteoglycans within the arterial intima.

Figure 1:
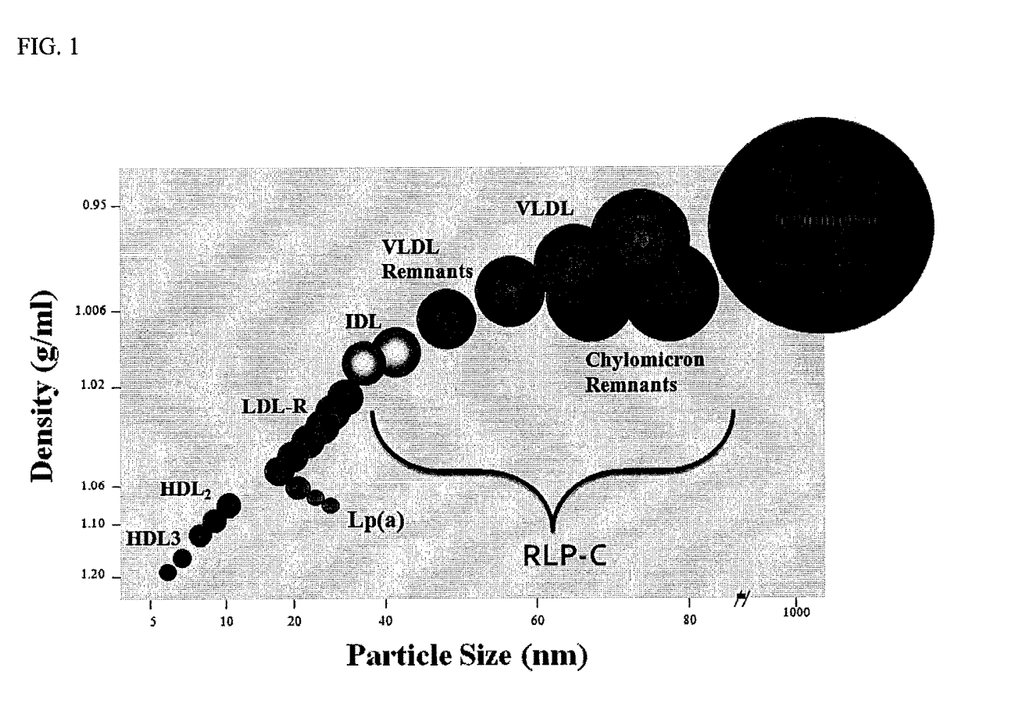
FIG. 1 shows the spectrum of lipoproteins, illustrating the density and size differences between various particle classes.

Confounding the analysis of remnant lipoproteins and their impact on disease is the difficulty in accurately measuring remnant particles. Remnants are formed in the circulation when apoB-48 containing chylomicrons of intestinal origin or apoB-100 containing VLDL of hepatic origin are converted by lipoprotein lipase (and to a lesser extent by hepatic lipase) into smaller and more dense particles (see FIG. 1). Compared with their precursors, remnant lipoproteins are depleted of triglyceride, phospholipid, and apo Cs (and apoA-I and apoA-IV in the case of chylomicrons) and are enriched in cholesteryl esters and apoE. As a result, remnant lipoproteins can be identified, separated and/or quantified in plasma on the basis of their density, charge, size, specific lipid components, apolipoprotein composition, or apolipoprotein immunospecificity. However, each of the approaches is subject to limitations for the following reasons. First, despite their reduced size and triglyceride content, remnants are difficult to differentiate from their triglyceride-rich precursors. Second, in many cases (absent disease and other complications) the remnant lipoproteins are rapidly catabolized and exist in the plasma at very low concentrations. Third, since remnant lipoproteins are a heterogeneous class of compounds that exist at various states of catabolism, remnants exist in a range of size and composition. For example, remnant lipoproteins become progressively smaller, more dense, and less negatively charged as they are converted from precursors to remnants. They gradually lose triglyceride and become enriched in cholesteryl ester. Remnant lipoproteins also lose C apolipoproteins (apoC-I, apoC-II, and apoC-III), which are replaced by apoE. At any given time, there is a continuous spectrum of different-sized remnant lipoproteins in the blood with different origins and different composition. Some of these particles are of intestinal origin. They contain apoB-48 and are more numerous after a fat-rich meal. The majority, however (in both the fed and fasted state), contain apoB-100 and are derived from the liver. Depending on the extent to which they have been lipolyzed, these species contain different proportions of triglyceride and cholesterol and may or may not contain apoCs or apoE. As a result, remnant lipoproteins are thus structurally and compositionally diverse.

Furthermore, in many studies the definition of remnant lipoproteins is not consistent, owing in a large part to the differences in isolation procedures and the heterogeneous nature of the particles themselves.

The present disclosure provides methods for predicting the risk of cardiovascular disease in a subject, methods for evaluating a subject for treatment for a cardiovascular disease and method for determining if a subject is suffering from a cardiovascular disease. Such methods were heretofore not appreciated in the art.

Methods

The present disclosure provides a variety of methods based on the determination of a remnant lipoprotein level in a subject or the cholesterol concentration in a remnant lipoprotein=in a subject. Such methods include, but are not limited to, a method of predicting the risk of cardiovascular disease, a method for evaluating a subject for treatment for a cardiovascular disease and method for determining if a subject is suffering from cardiovascular disease. In general, the methods described rely on determining a remnant lipoprotein level in a sample from a subject or determining the cholesterol concentration in a remnant lipoprotein in a sample from a subject.

The samples may be any sample described herein. In one embodiment, the sample is serum or plasma. Regardless of the source of the sample, in one embodiment the sample is subject to a fractionation protocol to separate the remnant lipoproteins in the sample. The remnant lipoproteins in the sample may be separated by any method known in the art. The present disclosure describes separation of remnant lipoproteins by ultracentrifugation. However, other methods may be used as is known in the art.

In one embodiment, the remnant lipoprotein levels is the particle number for the remnant lipoprotein. In such an embodiment, the particle number for the remnant lipoprotein is calculated. Exemplary methods are described herein for calculating particle number in the remnant lipoprotein. In another embodiment, the cholesterol concentration in the remnant lipoprotein is calculated. Exemplary methods are described herein for calculating cholesterol concentration in each remnant lipoprotein separated.

Methods for Predicting the Risk of Cardiovascular Disease

The present disclosure provides for methods for predicting the risk of cardiovascular disease in a subject, wherein the method comprises, consists of or consists essentially of determining a remnant lipoprotein level in the subject. The method may further comprise obtaining a sample from a subject.

In one embodiment of the methods described, the remnant lipoprotein level comprises, consists of or consists essentially of the level of IDL lipoprotein and one or more subsets of VLDL lipoprotein in the subject. Therefore the present disclosure provides a method for predicting the risk of cardiovascular disease in a subject by determining a remnant lipoprotein level in the subject, wherein the remnant lipoprotein level comprises, consists of or consists essentially of the level of IDL lipoprotein and one or more subsets of VLDL lipoprotein in the subject.

In another embodiment of the methods described, the one or more subsets of VLDL lipoprotein is VLDL3. Therefore the present disclosure provides a method for predicting the risk of cardiovascular disease in a subject by determining a remnant lipoprotein level in the subject, wherein the remnant lipoprotein level comprises, consists of or consists essentially of the level of IDL lipoprotein and VLDL3 lipoprotein in the subject.

In another embodiment of the methods described, the remnant lipoprotein level comprises, consists of or consists essentially of the level of IDL lipoprotein in the subject. Therefore the present disclosure provides a method for predicting the risk of cardiovascular disease in a subject by determining a remnant lipoprotein level in the subject, wherein the remnant lipoprotein level comprises, consists of or consists essentially of the level of IDL lipoprotein in the subject.

In another embodiment of the methods described, the remnant lipoprotein level comprises, consists of or consists essentially of the level of VLDL3 lipoprotein in the subject. Therefore the present disclosure provides a method for predicting the risk of cardiovascular disease in a subject by determining a remnant lipoprotein level in the subject, wherein the remnant lipoprotein level comprises, consists of or consists essentially of the level of VLDL3 lipoprotein in the subject.

In another embodiment of the methods described, the remnant lipoprotein level consists of or consists essentially of the level of IDL lipoprotein in the subject. Therefore the present disclosure provides a method for predicting the risk of cardiovascular disease in a subject by determining a remnant lipoprotein level in the subject, wherein the remnant lipoprotein level consists of or consists essentially of the level of IDL lipoprotein in the subject.

The above methods may also further include determining a cholesterol concentration in a remnant lipoprotein level in the subject as described herein.

The present disclosure also provides methods for predicting the risk of cardiovascular disease in a subject, wherein the method comprises, consists of or consists essentially of determining a cholesterol concentration in a remnant lipoprotein in the subject. The method may further comprise obtaining a sample from a subject.

In one embodiment of the methods described, the remnant lipoprotein comprises, consists of or consists essentially of IDL lipoprotein and one or more subsets of VLDL lipoprotein in the subject. Therefore the present disclosure provides a method for predicting the risk of cardiovascular disease in a subject by determining a cholesterol concentration in a remnant lipoprotein in the subject, wherein the remnant lipoprotein comprises, consists of or consists essentially of IDL lipoprotein and one or more subsets of VLDL lipoprotein in the subject.

In another embodiment of the methods described, the one or more subsets of VLDL lipoprotein is VLDL3. Therefore the present disclosure provides a method for predicting the risk of cardiovascular disease in a subject by determining a cholesterol concentration in a remnant lipoprotein in the subject, wherein the remnant lipoprotein comprises, consists of or consists essentially of IDL lipoprotein and VLDL3 lipoprotein in the subject.

In another embodiment of the methods described, the remnant lipoprotein comprises, consists of or consists essentially of IDL lipoprotein in the subject. Therefore the present disclosure provides a method for predicting the risk of cardiovascular disease in a subject by determining a cholesterol concentration in a remnant lipoprotein in the subject, wherein the remnant lipoprotein comprises, consists of or consists essentially of IDL lipoprotein in the subject.

In another embodiment of the methods described, the remnant lipoprotein comprises, consists of or consists essentially of VLDL3 lipoprotein in the subject. Therefore the present disclosure provides a method for predicting the risk of cardiovascular disease in a subject by determining a cholesterol concentration in a remnant lipoprotein in the subject, wherein the remnant lipoprotein comprises, consists of or consists essentially of VLDL3 lipoprotein in the subject.

In another embodiment of the methods described, the remnant lipoprotein consists of or consists essentially of IDL lipoprotein in the subject. Therefore the present disclosure provides a method for predicting the risk of cardiovascular disease in a subject by determining a cholesterol concentration in a remnant lipoprotein in the subject, wherein the remnant lipoprotein consists of or consists essentially of IDL lipoprotein in the subject.

The above methods may also further include determining a remnant lipoprotein level in the subject as described herein.

In the methods for predicting the risk of cardiovascular disease in a subject, an increase in level of remnant lipoproteins indicates the subject is at increased risk for cardiovascular disease. Such an increase in level of remnant lipoproteins may be determined with respect to the levels of IDL and one or more subclasses of VLDL, with respect to the levels of IDL and VLDL3, with respect to the levels of IDL alone or with respect to the levels of VLDL3 alone. In one embodiment, the foregoing is determined with respect to the levels of IDL and VLDL3. In another embodiment, the increased risk is determined with respect to the levels of IDL alone. In another embodiment, the increased risk is determined with respect to the levels of VLDL3 alone.

In the methods for predicting the risk of cardiovascular disease in a subject, an increase in cholesterol concentration as measured in the remnant lipoprotein indicates the subject is at increased risk for cardiovascular disease. Such an increase cholesterol concentration as measured in the remnant lipoprotein may be determined with respect to the levels of IDL and one or more subclasses of VLDL, with respect to IDL and VLDL3, with respect to IDL alone or with respect to VLDL3 alone. In one embodiment, the increased risk is determined with respect to the cholesterol concentration as measured in IDL and VLDL3. In another embodiment, the increased risk is determined with respect to the cholesterol concentration as measured in IDL alone. In another embodiment, the increased risk is determined with respect to the cholesterol concentration as measured in VLDL3 alone. In one embodiment, a cholesterol concentration of greater than 20 mg/dl in the IDL lipoprotein indicates a subject is an increased risk for cardiovascular disease. In one embodiment, a cholesterol concentration of greater than 10 mg/dl in the VLDL3 lipoprotein indicates a subject is at an increased risk for cardiovascular disease. In one embodiment, a cholesterol concentration of greater than 30 mg/dl in the IDL plus VLDL3 lipoprotein indicates a subject is an increased risk for cardiovascular disease.

Methods for Evaluating a Subject for Treatment for a Cardiovascular Disease

The present disclosure provides methods for evaluating a subject for treatment for a cardiovascular disease wherein the method comprises, consists of or consists essentially of determining a remnant lipoprotein level in the subject. The method may further comprise obtaining a sample from a subject.

In one embodiment of the methods described, the remnant lipoprotein level comprises, consists of or consists essentially of the level of IDL lipoprotein and one or more subsets of VLDL lipoprotein in the subject. Therefore the present disclosure provides a method for evaluating a subject for treatment for a cardiovascular disease by determining a remnant lipoprotein level in the subject, wherein the remnant lipoprotein level comprises, consists of or consists essentially of the level of IDL and one or more subsets of VLDL lipoprotein in the subject.

In another embodiment of the methods described, the one or more subsets of VLDL lipoprotein is VLDL3. Therefore the present disclosure provides a method for evaluating a subject for treatment for a cardiovascular disease by determining a remnant lipoprotein level in the subject, wherein the remnant lipoprotein level comprises, consists of or consists essentially of the level of IDL lipoprotein and VLDL3 lipoprotein in the subject.

In another embodiment of the methods described, the remnant lipoprotein level comprises, consists of or consists essentially of the level of IDL lipoprotein in the subject. Therefore the present disclosure provides a method for evaluating a subject for treatment for a cardiovascular disease by determining a remnant lipoprotein level in the subject, wherein the remnant lipoprotein level comprises, consists of or consists essentially of the level of IDL lipoprotein in the subject.

In another embodiment of the methods described, the remnant lipoprotein level comprises, consists of or consists essentially of the level of VLDL3 lipoprotein in the subject. Therefore the present disclosure provides a method for evaluating a subject for treatment for a cardiovascular disease by determining a remnant lipoprotein level in the subject, wherein the remnant lipoprotein level comprises, consists of or consists essentially of the level of VLDL3 lipoprotein in the subject.

In another embodiment of the methods described, the remnant lipoprotein level consists of or consists essentially of the level of IDL lipoprotein in the subject. Therefore the present disclosure provides a method for evaluating a subject for treatment for a cardiovascular disease by determining a remnant lipoprotein level in the subject, wherein the remnant lipoprotein level consists of or consists essentially of the level of IDL lipoprotein in the subject.

The above methods may also further include determining a cholesterol concentration in a remnant lipoprotein level in the subject as described herein.

The present disclosure also provides methods for evaluating a subject for treatment for a cardiovascular disease, wherein the method comprises, consists of or consists essentially of determining a cholesterol concentration in a remnant lipoprotein in the subject. The method may further comprise obtaining a sample from a subject.

In one embodiment of the methods described, the remnant lipoprotein comprises, consists of or consists essentially of IDL lipoprotein and one or more subsets of VLDL lipoprotein in the subject. Therefore the present disclosure provides a method for evaluating a subject for treatment for a cardiovascular disease by determining a cholesterol concentration in a remnant lipoprotein in the subject, wherein the remnant lipoprotein comprises, consists of or consists essentially of IDL lipoprotein and one or more subsets of VLDL lipoprotein in the subject.

In another embodiment of the methods described, the one or more subsets of VLDL lipoprotein is VLDL3. Therefore the present disclosure provides a method for evaluating a subject for treatment for a cardiovascular disease by determining a cholesterol concentration in a remnant lipoprotein in the subject, wherein the remnant lipoprotein comprises, consists of or consists essentially of IDL lipoprotein and VLDL3 lipoprotein in the subject.

In another embodiment of the methods described, the remnant lipoprotein comprises, consists of or consists essentially of IDL lipoprotein in the subject. Therefore the present disclosure provides a method for evaluating a subject for treatment for a cardiovascular disease by determining a cholesterol concentration in a remnant lipoprotein in the subject, wherein the remnant lipoprotein comprises, consists of or consists essentially of IDL lipoprotein in the subject.

In another embodiment of the methods described, the remnant lipoprotein comprises, consists of or consists essentially of VLDL3 lipoprotein in the subject. Therefore the present disclosure provides a method for evaluating a subject for treatment for a cardiovascular disease by determining a cholesterol concentration in a remnant lipoprotein in the subject, wherein the remnant lipoprotein comprises, consists of or consists essentially of VLDL3 lipoprotein in the subject.

In another embodiment of the methods described, the remnant lipoprotein consists of or consists essentially of IDL lipoprotein in the subject. Therefore the present disclosure provides a method for evaluating a subject for treatment for a cardiovascular disease by determining a cholesterol concentration in a remnant lipoprotein in the subject, wherein the remnant lipoprotein consists of or consists essentially of IDL lipoprotein in the subject.

The above methods may also further include determining a remnant lipoprotein level in the subject as described herein.

In the methods for evaluating a subject for treatment for a cardiovascular disease, when the evaluation indicates an increase in the remnant lipoproteins level, the subject is at an increased risk for cardiovascular disease. As a result, a healthcare provider makes a decision regarding care of the subject. Such a decision may involve a decision to initiate treatment for a cardiovascular disease, a decision to initiate or increase monitoring of the subject for a cardiovascular disease, a decision to initiate preventive measures in the subject and/or a decision to initiate lifestyle changes in the subject to reduce the risk of cardiovascular disease. Such an increase in level of remnant lipoproteins may be determined with respect to the levels of IDL and one or more subclasses of VLDL, with respect to the levels of IDL and VLDL3, with respect to the levels of IDL alone or with respect to the levels of VLDL3 alone. In one embodiment, the foregoing is determined with respect to the levels of IDL and VLDL3. In another embodiment the foregoing is determined with respect to the levels of IDL alone. In another embodiment the foregoing is determined with respect to the levels of VLDL3 alone.

In one embodiment, the method for evaluating a subject for treatment for a cardiovascular disease involves determining if the remnant lipoprotein level is increased and initiating treatment in the subject for a cardiovascular disease if such level is increased.

In another embodiment, the method for evaluating a subject for treatment for a cardiovascular disease involves determining if the remnant lipoprotein level is increased and initiating or increasing monitoring of the health of the subject, particularly monitoring the health of the subject with respect to cardiovascular disease, if such level is increased.

In a further embodiment, the method for evaluating a subject for treatment for a cardiovascular disease involves determining if the remnant lipoprotein level is increased and initiating preventive measures in the subject if such level is increased.

In a further embodiment, the method for evaluating a subject for treatment for a cardiovascular disease involves determining if the remnant lipoprotein level is increased and initiating lifestyle changes in the subject to reduce the risk of cardiovascular disease if such level is increased.

In a further embodiment, the method for evaluating a subject for treatment for a cardiovascular disease involves determining if the remnant lipoprotein level is increased and taking at least one of the following actions if such level is increased: i) initiating treatment in the subject for a cardiovascular disease; ii) initiating or increasing monitoring of the health of the subject, particularly monitoring the health of the subject with respect to cardiovascular disease; iii) initiating preventive measures in the subject; and iv) initiating lifestyle changes in the subject to reduce the risk of cardiovascular disease. Any combination of the foregoing actions may be taken.

In the methods for evaluating a subject for treatment for a cardiovascular disease, when the evaluation indicates an increase in cholesterol concentration as measured in the remnant lipoprotein level, the subject is at an increased risk for cardiovascular disease. As a result, a healthcare provider makes a decision regarding care of the subject. Such a decision may involve a decision to initiate treatment for a cardiovascular disease, a decision to initiate or increase monitoring of the subject for a cardiovascular disease, a decision to initiate preventive measures in the subject and/or a decision to initiate lifestyle changes in the subject to reduce the risk of cardiovascular disease. Such an increase cholesterol concentration as measured in the remnant lipoprotein may be determined with respect to IDL and one or more subclasses of VLDL, with respect to IDL and VLDL3, with respect to IDL alone or with respect to VLDL3 alone. In one embodiment, the increased risk is determined with respect to the cholesterol concentration as measured in IDL and VLDL3. In another embodiment, foregoing is determined with respect to the cholesterol concentration as measured in IDL alone. In another embodiment, foregoing is determined with respect to the cholesterol concentration as measured in VLDL3 alone. In one embodiment, a cholesterol concentration of greater than 20 mg/dl in the IDL lipoprotein indicates a subject is an increased risk for cardiovascular disease and the subject is a candidate for treatment. In one embodiment, a cholesterol concentration of greater than 10 mg/dl in the VLDL3 lipoprotein indicates a subject is at an increased risk for cardiovascular disease and the subject is a candidate for treatment. In one embodiment, a cholesterol concentration of greater than 30 mg/dl in the IDL plus VLDL3 lipoprotein indicates a subject is an increased risk for cardiovascular disease and the subject is a candidate for treatment.

In one embodiment, the method for evaluating a subject for treatment for a cardiovascular disease involves determining if the cholesterol concentration in the remnant lipoprotein is increased and initiating treatment in the subject for a cardiovascular disease if such concentration is increased.

In another embodiment, the method for evaluating a subject for treatment for a cardiovascular disease involves determining if the cholesterol concentration in the remnant lipoprotein is increased and initiating or increasing monitoring of the health of the subject, particularly monitoring the health of the subject with respect to cardiovascular disease, if such concentration is increased.

In a further embodiment, the method for evaluating a subject for treatment for a cardiovascular disease involves determining if the cholesterol concentration in the remnant lipoprotein is increased and initiating preventive measures in the subject if such concentration is increased.

In a further embodiment, the method for evaluating a subject for treatment for a cardiovascular disease involves determining if the cholesterol concentration in the remnant lipoprotein is increased and initiating lifestyle changes in the subject to reduce the risk of cardiovascular disease if such concentration is increased.

In a further embodiment, the method for evaluating a subject for treatment for a cardiovascular disease involves determining if the cholesterol concentration in a remnant lipoprotein is increased and taking at least one of the following actions if such level is increased: i) initiating treatment in the subject for a cardiovascular disease; ii) initiating or increasing monitoring of the health of the subject, particularly monitoring the health of the subject with respect to cardiovascular disease; iii) initiating preventive measures in the subject; and iv) initiating lifestyle changes in the subject to reduce the risk of cardiovascular disease. Any combination of the foregoing actions may be taken.

Methods for Determining if a Subject is Suffering from a Cardiovascular Disease

The present disclosure provides methods for determining if a subject is suffering from a cardiovascular disease wherein the method comprises, consists of or consists essentially of determining a remnant lipoprotein level in the subject. The method may further comprise obtaining a sample from a subject.

In one embodiment of the methods described, the remnant lipoprotein level comprises, consists of or consists essentially of the level of IDL lipoprotein and one or more subsets of VLDL lipoprotein in the subject. Therefore the present disclosure provides a method for determining if a subject is suffering from a cardiovascular disease by determining a remnant lipoprotein level in the subject, wherein the remnant lipoprotein level comprises, consists of or consists essentially of the level of IDL lipoprotein and one or more subsets of VLDL lipoprotein in the subject.

In another embodiment of the methods described, the one or more subsets of VLDL lipoprotein is VLDL3. Therefore the present disclosure provides a method for determining if a subject is suffering from a cardiovascular disease by determining a remnant lipoprotein level in the subject, wherein the remnant lipoprotein level comprises, consists of or consists essentially of the level of IDL lipoprotein and VLDL3 lipoprotein in the subject.

In another embodiment of the methods described, the remnant lipoprotein level comprises, consists of or consists essentially of the level of IDL lipoprotein in the subject. Therefore the present disclosure provides a method for determining if a subject is suffering from a cardiovascular disease by determining a remnant lipoprotein level in the subject, wherein the remnant lipoprotein level comprises, consists of or consists essentially of the level of IDL lipoprotein in the subject.

In another embodiment of the methods described, the remnant lipoprotein level comprises, consists of or consists essentially of the level of VLDL3 lipoprotein in the subject. Therefore the present disclosure provides a method for determining if a subject is suffering from a cardiovascular disease by determining a remnant lipoprotein level in the subject, wherein the remnant lipoprotein level comprises, consists of or consists essentially of the level of VLDL3 lipoprotein in the subject.

In another embodiment of the methods described, the remnant lipoprotein level consists of or consists essentially of the level of IDL lipoprotein in the subject. Therefore the present disclosure provides a method for determining if a subject is suffering from a cardiovascular disease by determining a remnant lipoprotein level in the subject, wherein the remnant lipoprotein level consists of or consists essentially of the level of IDL lipoprotein in the subject.

The above methods may also further include determining a cholesterol concentration in a remnant lipoprotein level in the subject as described herein.

The present disclosure also provides methods for determining if a subject is suffering from a cardiovascular disease, wherein the method comprises, consists of or consists essentially of determining a cholesterol concentration in a remnant lipoprotein in the subject. The method may further comprise obtaining a sample from a subject.

In one embodiment of the methods described, the remnant lipoprotein comprises, consists of or consists essentially of IDL lipoprotein and one or more subsets of VLDL lipoprotein in the subject. Therefore the present disclosure provides a method for determining if a subject is suffering from a cardiovascular disease by determining a cholesterol concentration in a remnant lipoprotein in the subject, wherein the remnant lipoprotein comprises, consists of or consists essentially of IDL lipoprotein and one or more subsets of VLDL lipoprotein in the subject.

In another embodiment of the methods described, the one or more subsets of VLDL lipoprotein is VLDL3. Therefore the present disclosure provides a method for determining if a subject is suffering from a cardiovascular disease by determining a cholesterol concentration in a remnant lipoprotein in the subject, wherein the remnant lipoprotein comprises, consists of or consists essentially of IDL lipoprotein and VLDL3 lipoprotein in the subject.

In another embodiment of the methods described, the remnant lipoprotein comprises, consists of or consists essentially of IDL lipoprotein in the subject. Therefore the present disclosure provides a method for determining if a subject is suffering from a cardiovascular disease by determining a cholesterol concentration in a remnant lipoprotein in the subject, wherein the remnant lipoprotein comprises, consists of or consists essentially of IDL lipoprotein in the subject.

In another embodiment of the methods described, the remnant lipoprotein comprises, consists of or consists essentially of VLDL3 lipoprotein in the subject. Therefore the present disclosure provides a method for determining if a subject is suffering from a cardiovascular disease by determining a cholesterol concentration in a remnant lipoprotein in the subject, wherein the remnant lipoprotein comprises, consists of or consists essentially of VLDL3 lipoprotein in the subject.

In another embodiment of the methods described, the remnant lipoprotein consists of or consists essentially of IDL lipoprotein in the subject. Therefore the present disclosure provides a method for determining if a subject is suffering from a cardiovascular disease by determining a cholesterol concentration in a remnant lipoprotein in the subject, wherein the remnant lipoprotein consists of or consists essentially of IDL lipoprotein in the subject.

The above methods may also further include determining a remnant lipoprotein level in the subject as described herein.

In the methods for determining if a subject is suffering from a cardiovascular disease, an increase in level of remnant lipoproteins indicates the subject is suffering from cardiovascular disease. Such an increase in level of remnant lipoproteins may be determined with respect to the levels of IDL and one or more subclasses of VLDL, with respect to the levels of IDL and VLDL3, with respect to the level of IDL alone or with respect to the level of VLDL3 alone. In one embodiment, the foregoing is determined with respect to the levels of IDL and VLDL3. In another embodiment, the foregoing is determined with respect to the level of IDL alone. In another embodiment, the foregoing is determined with respect to the level of VLDL3 alone.

In the methods for determining if a subject is suffering from a cardiovascular disease, an increase in cholesterol concentration as measured in the remnant lipoprotein indicates the subject is suffering from cardiovascular disease. Such an increase cholesterol concentration as measured in the remnant lipoprotein may be determined with respect to the levels of IDL and one or more subclasses of VLDL, with respect to the levels of IDL and VLDL3, with respect to IDL alone or with respect to VLDL3 alone. In one embodiment, the foregoing is determined with respect to the cholesterol concentration as measured in IDL and VLDL3. In another embodiment, the foregoing is determined with respect to the cholesterol concentration as measured in IDL remnant lipoprotein. In another embodiment, the foregoing is determined with respect to the cholesterol concentration as measured in VLDL3 remnant lipoprotein. In one embodiment, a cholesterol concentration of greater than 20 mg/dl in the IDL lipoprotein indicates a subject is suffering from cardiovascular disease. In one embodiment, a cholesterol concentration of greater than 10 mg/dl in the VLDL3 lipoprotein indicates a subject is suffering from cardiovascular disease. In one embodiment, a cholesterol concentration of greater than 30 mg/dl in the IDL plus VLDL3 lipoprotein indicates a subject is suffering from cardiovascular disease.

In the methods for predicting the risk of cardiovascular disease in a subject, for evaluating a subject for treatment for a cardiovascular disease and for determining if a subject is suffering from a cardiovascular disease, the following specific embodiments apply to each method.

In certain embodiments of the foregoing methods, the subject may be a mammal, such as a human. In one embodiment, the subject is a human. In another embodiment, the subject is a male. In a further embodiment the subject is a female. In still a further embodiment, the subject is a male or female over 50 years of age, over 55 years of age or over 60 years of age. In a further embodiment, the subject is an African American. In a further embodiment, the subject is a Caucasian. In a further embodiment, the subject (including any of the specific embodiments above) is asymptomatic for cardiovascular disease (for example, those subject who do not display current symptoms of cardiovascular disease; such determination may be made by a healthcare professional). In a further embodiment, the subject (including any of the specific embodiments above) has not experienced a myocardial infarction. In a further embodiment, the subject (including any of the specific embodiments above) is not currently taking lipid lowering medications.

In certain embodiments of the foregoing methods, the cardiovascular disease is as defined previously. In one embodiment, the cardiovascular disease is associated with hypertriglyceridemia. In a further embodiment the cardiovascular disease is myocardial infarction (MI), including acute MI. In a further embodiment, the cardiovascular disease is coronary heart disease or coronary artery disease. In a further embodiment, the cardiovascular disease is coronary death. In a further embodiment, the cardiovascular disease is coronary insufficiency. In a further embodiment, the cardiovascular disease is angina pectoris. In a further embodiment, the cardiovascular disease is atherosclerosis.

In certain embodiments of the foregoing methods, the remnant lipoprotein is isolated by separating the plurality of lipoproteins present in a sample from the subject. The remnant lipoprotein level may be determined based on the IDL and one or more subclasses of VLDL, IDL and VLDL3, IDL and/or VLDL3 content from the sample. The remnant lipoprotein level may be a determination of particle number, for example the number of particles of IDL and one or more subclasses of VLDL, IDL and VLDL3, IDL and/or VLDL3 in the sample.

In one embodiment, the lipoproteins in the sample are fractionated. In another embodiment, the lipoproteins in the sample are fractionated using centrifugation or ultracentrifugation. In such embodiments, a single class of lipoprotein (for example, IDL) may be present in a single fraction. In such a case, the lipoprotein level in the fraction is determined to obtain the lipoprotein level for such lipoprotein class. Furthermore, a single class of lipoprotein (for example, IDL) may be present in more than 1 fraction collected. In such a case, the lipoprotein level in the fractions are summed to obtain the lipoprotein level for such lipoprotein class. Still further, more than 1 lipoprotein class (for example, IDL and LDL) may be present in a single fraction collected. In such a case, the lipoprotein level for each class may be individually determined using methods as described herein or as known in the art to obtain the lipoprotein level for each lipoprotein class in the fraction; the final lipoprotein level may be determined by adding the lipoprotein level from additional fractions as discussed.

In certain embodiments of the foregoing methods, the cholesterol concentration in the remnant lipoprotein is determined by separating the plurality of lipoproteins present in a sample from the subject and determining the cholesterol concentration in the IDL and VLDL3, IDL and/or VLDL3 lipoproteins from the sample. The fractionation methods described above and elsewhere herein may be used.

Samples

A variety of samples may be obtained from a subject for use with the methods described herein. Suitable samples include, but are not limited to, blood, serum, plasma and other types of bodily tissue and fluid as is known in the art. In a specific embodiment, the sample is plasma or serum.

In one embodiment, the sample is a blood sample. Such a sample is collected as is known in the art, such as in a serum separator tube (SST) or plain red top serum tube. Serum is separated according to standard procedure and filtered to remove any clots, fibrin and any large interfering particles. The sample may then be subject to the methods disclosed herein.

Separation of Remnant Lipoproteins

Remnant lipoproteins, along with other lipoproteins, may be separated from one another in the sample by a variety of methods. As discussed above, remnant lipoproteins have characteristic chemical and physical properties. As a result, remnant lipoproteins can be separated or identified can thus be identified, separated, or quantified in plasma on the basis of their density, charge, size, specific lipid components, apolipoprotein composition, or apolipoprotein immunogenicity. Various techniques for the foregoing are described in Cohn et al. (Arteriosclerosis, Thrombosis and Vascular Biology (vol. 19, pp 2472-2486, 1999), which is incorporated by reference herein for such teachings.

In a particular embodiment, remnant lipoproteins are separated based on density. In a particular embodiment, when separated by density ultracentrifugation may be used. In one aspect, such ultracentrifugation is vertical spin density gradient ultracentrifugation. In another aspect, such ultracentrifugation is the vertical auto profile ultracentrifugation method (Atherotech; Birmingham, Ala.). The VAP method separates lipoproteins based on their density using single vertical spin density gradient ultracentrifugation (Kulkarni K R, et al., *J Lipid Res* 1994; 35: 159-168; Kulkarni K R., *Clin Lab Med,* 2006; 26: 787-802; the foregoing references are incorporated herein by reference for the teaching of the VAP method). Such methods are described in U.S. Pat. No. 5,633,168 and U.S. patent application Ser. No. 11/316,520 (which are hereby incorporated by reference for such teaching). Furthermore, the VAP technology also measures cholesterol levels in each of the separated fractions in a single method. However, any ultracentrifugation method known in the art may be used. In this method, the cholesterol concentration in each remnant lipoprotein fraction is calculated.

In another embodiment, the remnant lipoproteins are separated and a remnant lipoprotein particle number is determined as described in PCT/US13/46170 (which is hereby incorporated by reference for such teaching). The methods described also utilizes single vertical spin density gradient ultracentrifugation. In this method the particle number for each remnant lipoprotein fraction is calculated. The separated remnant lipoprotein fractions may be subject to cholesterol testing if desired using methods known in the art. The methods described for determining particle number for each remnant lipoprotein fraction may also be combined with the methods for determining cholesterol concentration in each lipoprotein remnant fraction to determine both parameters.

The measurement of remnant lipoprotein particle concentration (number) is based on the direct relationship between the number of lipoprotein particles present in a given volume of sample and the area under the lipoprotein peak as determined by a detector. During the separation step, (such as, but not limited to, ultracentrifugation, such as using the VAP technology) lipoproteins are separated based upon their respective densities. When ultracentrifugation is used in the separation step, the HDL migrates to the bottom of the centrifuge tube, LDL migrates to the middle of the tube, and VLDL migrates to the top of tube (various subclasses of VLDL are also separated, such as but not limited to VLDL3). Lp(a) migrates between HDL and LDL, and IDL migrates between LDL and VLDL. Thus, as lipoproteins elute sequentially from the bottom of the centrifuge tube and pass through the detector (such as photometric detector or a light scattering detector as discussed in more detail herein), a signal is generated by the detector. The signal from the detector is output as a continuous curve corresponding to particle concentration profile, with peaks corresponding to the various lipoproteins (including HDL and other proteins, Lp(a), LDL, IDL, and VLDL) that are present in the sample.

Using density gradient ultracentrifugation, the lipoprotein particles in a sample are separated in the following order (from the bottom of the density gradient to the top of the density gradient): HDL, Lp(a), LDL, IDL and VLDL (including subclasses thereof). A variety of density gradient ultracentrifugation conditions may be used. The composition of the density gradient may impact the separation between various lipoprotein species. The following are illustrated by way of example only and should not be interpreted as limiting the scope of the separation techniques to density gradient ultracentrifugation or as limiting the conditions employed in density gradient ultracentrifugation to those conditions specified.

As discussed above, in some cases certain a given fraction may contain more than one type of serum lipoprotein. Specific density gradient ultracentrifugation conditions may be employed to provide maximum resolution of the various lipoprotein classes (such as for example, LDL, IDL and VLDL or HDL and Lp(a)), including remnant lipoproteins (such as for example, IDL and VLDL. And subclasses thereof, for example VLDL3) or may be employed to provide maximum resolution of a single lipoprotein (such as IDL and/or VLDL/VLDL3).

In one embodiment, the density gradient ultracentrifugation conditions and parameters are varied to provide maximum resolution of each of the various lipoprotein classes and/or the remnant lipoproteins, such as IDL and VLDL3. In another embodiment, the density gradient ultracentrifugation conditions and parameters are varied to provide maximum resolution of one or more specific lipoprotein classes, such as IDL and VLDL3. In still another embodiment, the density gradient ultracentrifugation conditions and parameters are varied to provide maximum resolution of VLDL3. In still another embodiment, the density gradient ultracentrifugation conditions and parameters are varied to provide maximum resolution of IDL.

Conditions and parameters that may be varied include, but are not limited to, density of the layers comprising the density gradient, volume of the layers comprising the density gradient, centrifugation time settings, acceleration setting (impacting the time it takes for the centrifuge to reach a set RPM), deceleration settings (impacting the time it takes for the centrifuge to come to a stop from the set RPM at the end a specified time setting), speed of the centrifuge (measured in revolutions per minute, RPM, or relative centrifugal force, RCF; RCF and RPM are related by the equation $RCF=1.1118\times10^{-5}\times r\times rpm^2$, where r is the rotor radius in centimetres) and temperature of the centrifugation run. The various parameters discussed above may be varied singly or in any combination desired.

In one embodiment, the density gradient comprises two layers of gradient material (referred to as a top and bottom layer). A commonly used density gradient material is KBr. Other commonly used density gradient materials include cesium chloride, sucrose, and colloidal silica particles coated with polyvinylpyrrolidone (such as the product sold as Percoll®). Any density gradient solution known in the art to create the required density range may be used. Centrifugation will be performed in an appropriate vessel, such as a centrifuge tube. A variety of suitable centrifuge tubes are commercially available, for example from Beckman-Coulter, of Brea, Calif. In a specific embodiment separation is achieved using a single spin.

In one aspect of this embodiment, the density of the bottom layer ranges from 1.10 to 1.40 g/ml, from 1.15 to 1.30 g/ml or from 1.15 to 1.25 g/ml and the density of the top layer ranges from 0.5 to 1.2 g/ml, from 1.0 to 1.15 g/ml or from 1.0 to 1.10 g/ml. In another aspect of this embodiment, the density of the bottom layer is 1.21 g/ml or 1.30 g/ml and the density of the top layer is 1.05 g/ml. Further, in one aspect of this embodiment, the volume of the bottom layer ranges from 0.2 to 4.0 ml, from 0.8 to 2.5 ml or from 1 to 2 ml and the volume of the top layer ranges from 1 to 4.8 ml, from 1.2 ml to 3.0 ml or from 3.0 to 4.0 ml. In another aspect of this embodiment, the volume of the bottom layer is 2.0 ml or 1.0 ml and the volume of the top layer is 2.90 ml or 3.9 ml.

Further, in one aspect of this embodiment, the settings for the ultracentrifuge are varied as follow: (i) centrifugation time from 10 to 70 minutes (note that centrifugation time does not include the time required for acceleration and deceleration of the centrifuge rotor), from 15 to 50 minutes or from 20 to 40 minutes; (ii) centrifugation speed from 50,000 RPM to 75,000 RPM or 60,000 to 70,000 RPM; or from $200,000\times g$ to $550,000\times g$ or $300,000\times g$ to $480,000\times g$ and (iii) centrifugation temperature from 15 to 30 degrees Celsius or from 20 to 25 degrees Celsius.

Furthermore, in one aspect of this embodiment, the acceleration and deceleration settings are selected provide appropriate acceleration and deceleration profiles in order to maximize the desired separation. In one aspect, the acceleration and/or deceleration phases of the spin are set to be slow in order to minimize vibrations that may occur during a quick acceleration and/or deceleration. In one aspect, the acceleration and/or deceleration phases of the spin are set to be fast in order to resolve a given class of lipoprotein; faster acceleration and/or deceleration settings may be used when the density/volume of one or more layers of the density gradient, particularly the bottom layer, is increased 1.25 g/ml or 1.0 ml, respectively. For example, using a Beckman Coulter ultracentrifuge (Optima™ XL-100 K Ultracentrifuge), the acceleration and/or deceleration settings may range from 5 to 9 or 8 to 9 (with 9 being the slowest setting). In another aspect of this embodiment, the acceleration and/or deceleration settings may range from 1 to 5 or 2 to 4 (with 1 being the fastest setting).

In one embodiment applicable for general separation of lipoproteins from a sample, the following conditions are used (using a Beckman Coulter Optima XL 100 ultracentrifuge with a Beckman Vertical Rotor (VTi 65.2)).

| Condition 1 | |
|---|---|
| Bottom Layer KBr Density | 1.21 g/mL |
| Top Layer KBr Density | 1.004 g/mL |
| Bottom Layer Volume | 1.426 mL |
| Top Layer Volume | 3.56 mL |
| Centrifugation Time Setting | 36 minutes |
| Acceleration Settings | 6 |
| Deceleration Settings | 6 |
| Centrifugation Speed | 65000 rpm |
| Centrifugation Temperature | 23° C. |

As discussed herein, specific ultracentrifugation conditions may be used to maximize separation of a specific lipoprotein from one or more other lipoproteins.

In a particular embodiment, the density gradient ultracentrifugation conditions are used to provide maximum resolution of LDL and IDL lipoproteins. In one embodiment, the following centrifugations conditions are used when to isolate IDL (using a Beckman Coulter Optima XL 100 ultracentrifuge with a Beckman Vertical Rotor (VTi 65.2)).

| Condition 2 | |
|---|---|
| Bottom Layer KBr Density | 1.21 g/mL |
| Top Layer KBr Density | 1.05 g/mL |
| Bottom Layer Volume | 1.0 mL |
| Top Layer Volume | 3.94 mL |
| Centrifugation Time Setting | 20 minutes |
| Acceleration Settings | 9 |
| Deceleration Settings | 9 |
| Centrifugation Speed | 65000 rpm |
| Centrifugation Temperature | 23° C. |

EXAMPLES

Sample Collection and Separation

A blood sample is collected from the subject. Such a sample is collected as is known in the art, such as in a serum separator tube (SST) or plain red top serum tube. Serum is separated according to standard procedure and filtered to remove any clots, fibrin and any large interfering particles.

In one embodiment, samples are subject to density gradient centrifugation to separate lipid components. Density gradients were prepared using either manual pipette and dispensing devices or an automated liquid handler (such as the Tecan Genesis™). Multiple serum samples may be processed at one time. In one embodiment, a batch consisting of 16 serum samples is simultaneously prepared using an automated liquid handler. The following steps were used in the following examples:

1. Pipette 50 μL serum and mix with 1950 μL of 1.21 g/mL KBr solution.
2. Pipette 3.56 mL of 1.004 g/mL saline solution into a 5 mL Beckman centrifuge tube.
3. Slowly underlay 1.4256 ml of above prepared serum: KBr mixture to prepare a two density layer gradient.

Once the density gradient was prepared, all 16 centrifuge tubes with density gradients were placed in a Beckman Vertical Rotor (VTi 65) and centrifuged at 65,000 rpm for 47 minutes (including acceleration and deceleration) using a Beckman Coulter Optima XL 100 ultracentrifuge.

Example 1—Remnant Lipoproteins Predicts MI Risk

The Jackson Heart Study (JHS) was set-up to investigate possible causes behind the elevated risk of CVD. The JHS was a prospective, population-based, longitudinal study which enrolled over 5,300 African American subjects from the Jackson, Miss. region that were free from prior cardiovascular disease. Subjects were followed for adjudicated coronary heart disease events including death, myocardial infarction, and revascularizations. In addition, a multitude of sociodemographic variables and biological markers were collected at baseline as well as in scheduled follow-up visits. The age range of subjects was from 35 to 84 years of age. The mean age was 54.9 years (SD of 12.8 years) with a median age of 55 years. Median follow-up was 5.7 years.

Of the 5,300 subject cohort, 4,722 subjects were subject to lipoprotein evaluations obtained during baseline visits. Fasting serum samples were obtained and lipoproteins characterized using the VAP methodology. Briefly, the VAP methodology uses a vertical density gradient, ultra centrifugation technique that directly measures the cholesterol concentration of all 5 major lipoprotein classes along with quantitation of the lipid subclasses. VAP is based upon the use of a salt density gradient to separate the lipids in a diluted serum sample. The gradient is subjected to a single vertical spin density-gradient ultra-centrifugation. The separated lipoprotein classes are then continuously drained from the bottom of the centrifuge tube into a continuous flow analyzer where they sequentially react with a cholesterol-specific enzymatic reagent producing a concentration-dependent lipoprotein absorbance profile monitored by a spectrophotometer. The digital output from the spectrophotometer is collected by a computer and the resulting absorbance curve is deconvoluted to quantify individual lipoprotein classes (HDL-C, Lp(a)-C, LDL-C, IDL-C and VLDL-C and their subclasses) using proprietary software. For this study, remnant lipoproteins were defined as VLDL3 and IDL and the cholesterol concentrations, VLD3-C and IDL-C, in each were determined.

Cox proportional hazard models were used to examine the relationship between lipoproteins and acute myocardial infarctions (AMI) in an un-adjusted and fully adjusted model. In the adjusted model, adjustments were made for traditional cardiovascular risk factors such as blood pressure, diabetes, smoking as well as age, sex, BMI, lipid therapy and education.

Table 1 shows basic demographic and sociodemographic characteristics of the cohort. Amongst the 4,722 participants over a median follow up of 5.7 years (maximum 8.2 yrs), 78 AMIs were reported. When comparing the baseline characteristics of the two groups (with and without AMI) without any adjustment, those who developed AMI, were older, more likely to have diabetes, elevated systolic BP and be current or previous smokers (which is consistent with previous results).

TABLE 1

| Variable | No AMI (n = 4,614) | AMI (n = 78) | p-value |
| --- | --- | --- | --- |
| Age (years) | 54.08 (12.79) | 64.14 (9.55) | <0.001 |
| Gender, Female | 2969 (64%) | 49 (63%) | 0.839 |
| Diabetes | 772 (17%) | 38 (49%) | <0.001 |
| Systolic BP | 126.57 (18.20) | 136.19 (21.22) | <0.001 |
| Diastolic BP | 79.02 (10.42) | 77.38 (10.47) | 0.169 |
| BMI | 31.79 (7.29) | 30.09 (6.01) | 0.042 |

TABLE 1-continued

| Variable | No AMI (n = 4,614) | AMI (n = 78) | p-value |
| --- | --- | --- | --- |
| Waist Circumference | 100.60 (16.27) | 101.25 (14.32) | 0.729 |
| Education | | | |
| <High School | 776 (17%) | 22 (29%) | 0.005 |
| High School/GED | 1962 (42%) | 35 (45%) | 0.005 |
| College | 1888 (41%) | 20 (26%) | 0.005 |
| Smoking Status | | | |
| Never | 3193 (69%) | 43 (55%) | 0.009 |
| Former | 821 (18%) | 24 (31%) | 0.009 |
| Current | 595 (13%) | 11 (14%) | 0.009 |
| Alcohol Use | 2168 (47%) | 28 (36%) | 0.053 |
| Lipid-altering Meds | 473 (11%) | 17 (24%) | 0.001 |

Table 2 shows an analysis of the baseline lipids of those with and without AMI, evaluating total remnant lipoprotein-cholesterol (RLPc; cholesterol in the IDL and VLDL3 levels), IDL cholesterol (IDLc), VLDL3 cholesterol (VLDL3c), total cholesterol (Total C), LDL cholesterol (LDLc), HDL cholesterol (HDLc), triglycerides, Apolipoprotein A1 (ApoA1) and apolipoprotein B (ApoB). Table 2 shows that those subjects with confirmed AMI had higher levels of ApoB (the atherogenic particle), which drove the higher ApoB/ApoA1 observed. In addition, statistically significant increases in the levels of RLPc, IDLc and VLDLc were also observed. Increases in LDLc and triglycerides were seen, but these increases did not reach statistical significance.

TABLE 2

| Variable | No AMI (n = 4,614) | AMI (n = 78) | p-value |
| --- | --- | --- | --- |
| RLPc | 29.7 (11.97) | 34.77 (14.00) | <0.001 |
| IDLc | 16.4 (7.95) | 19.67 (9.05) | <0.001 |
| VLDL3c | 13.3 (4.71) | 15.10 (5.94) | 0.001 |
| Total C | 198.4 (40.27) | 206.00 (46.93) | 0.10 |
| HDLc | 53.4 (14.45) | 52.36 (14.98) | 0.51 |
| LDLc | 122.6 (36.07) | 128.23 (39.72) | 0.17 |
| Triglycerides | 109.6 (100.49) | 125.71 (87.35) | 0.16 |
| ApoA1 | 152.6 (23.58) | 150.99 (25.20) | 0.54 |
| ApoB | 97.4 (23.01) | 103.78 (25.18) | 0.02 |
| ApoB/ApoA1 | 0.65 (0.19) | 0.7 (0.17) | 0.04 |

Figure 2:
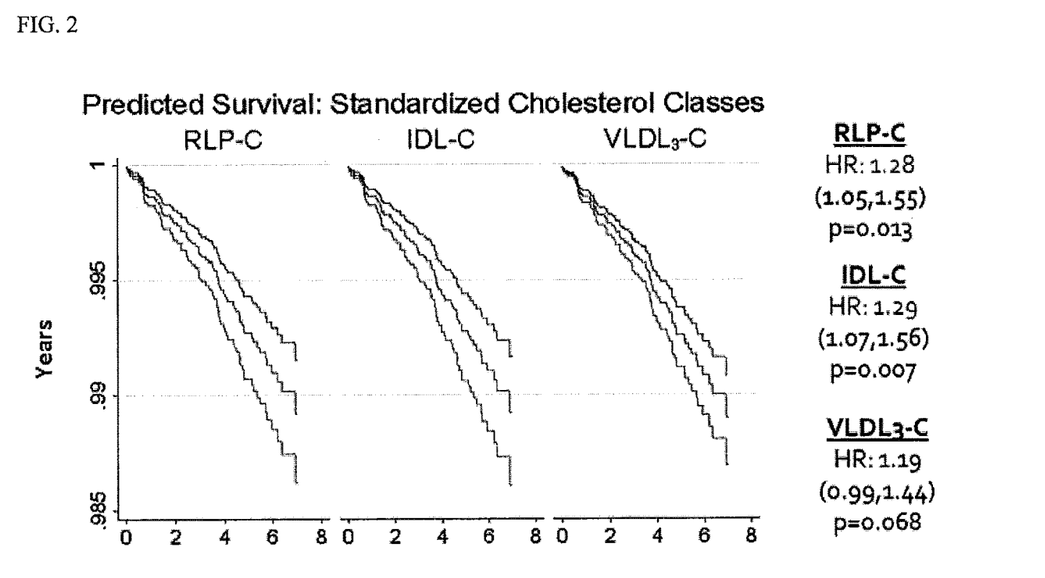
FIG. 2 shows the association of remnant lipoproteins with acute myocardial infarction in a fully adjusted model.

Table 3 shows the hazard ratios for a 1 standard deviation increase for selected lipoproteins in both the un-adjusted and adjusted models. As can be seen in Table 3, in the unadjusted model, a 1 standard deviation increase in RLPc, IDLc and VLDL3c was associated with hazard ratios of 1.41, 1.41 and 1.33, respectively (all statistically significant with p values less than or equal to 0.001). In the fully adjusted model (adjusted for age, sex, BMI, systolic & diastolic blood pressure, diabetes, smoking, lipid lowering medications and education), a 1 standard deviation increase in RLPc and IDLc was associated with a hazard ratio of 1.28 and 1.29 respectively (which was statistically significant with p values of 0.013 and 0.007, respectively). In contrast, a 1 standard deviation increase in small VLDL3c lost its significance in the fully adjusted model (hazard ration of 1.19 with a p value of 0.068). FIG. 2 shows the results graphically, illustrating that an increase in both RLPc and IDLc with associated with decreased survival. In FIG. 2, the middle line in each graph indicates the mean, with the line above and below the middle representing minus 1 standard deviation and plus 1 standard deviation, respectively.

TABLE 3

|  | Unadjusted | Fully Adjusted |
| --- | --- | --- |
| RLP-C | 1.41 | 1.28 |
|  | (1.19, 1.68) | (1.05, 1.55) |
|  | p < 0.001 | p = 0.013 |
| IDL-C | 1.41 | 1.29 |
|  | (1.18, 1.69) | (1.07, 1.56) |
|  | p < 0.001 | p = 0.007 |
| VLDL3-C | 1.33 | 1.19 |
|  | (1.13, 1.57) | (0.99, 1.44) |
|  | p = 0.001 | p = 0.068 |

Figure 3:
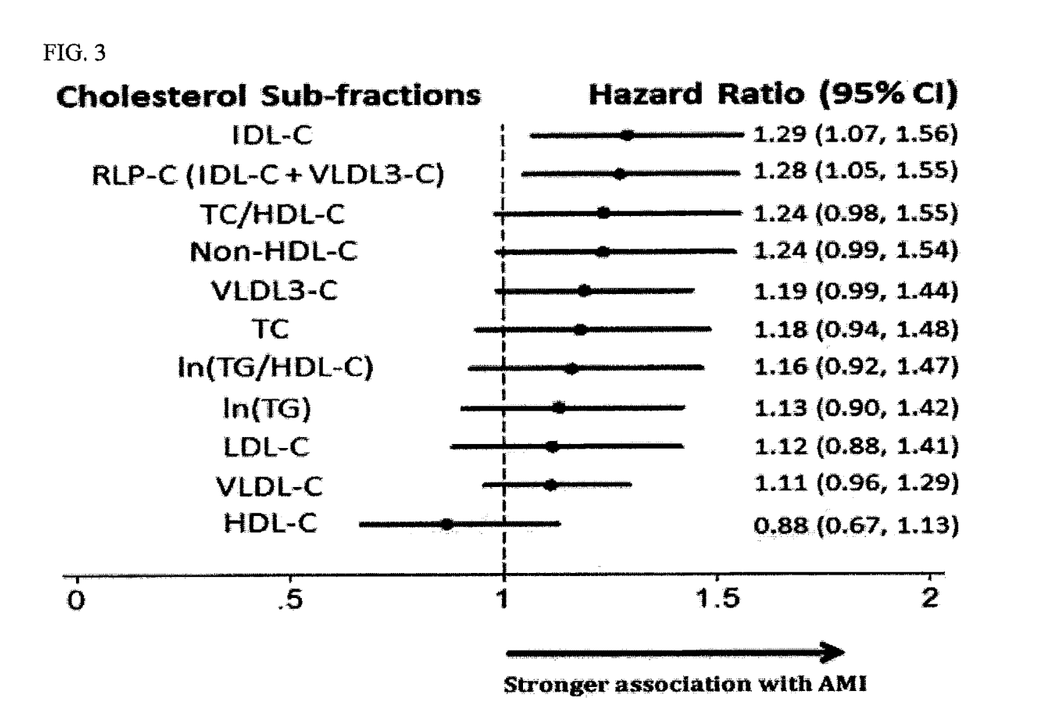
FIG. 3 shows the hazard ratios for various lipoprotein subclasses for association with acute myocardial infarction in a fully adjusted model.

FIG. 3 shows a forest plot of associations of various cholesterol subfractions with the development of AMI. FIG. 3 demonstrates that, in a fully adjusted model, RLPc and IDLc were strongly associated with development of AMI. A similar positive association was seen for VLDL3c, but did not reach significance. Of particular interest is that traditional markers of risk, such as LDLc and non-HDLc, while demonstrating a non-significant trend towards AMI, did not show as strong an association with AMI as RLPc and IDLc.

Example 2—Remnant Lipoproteins Predict CHD Risk

Like the JHS, the Framingham Offspring Cohort Study (FOCS) investigated possible causes behind the elevated risk of CHD. The Framingham Offspring Cohort Study (FOCS) is a longitudinal study initiated in 1971 with a sample of 5,135 offspring of the original Framingham Heart Study (FHS) cohort. The Offspring Study is composed of the children (and their spouses) of the members of the original Framingham Study cohort. The Offspring population has a broader age range and an average age that is approximately 30 years younger than the original parent cohort.

819 serum specimens from FOCS participants not on lipid medication who underwent a medical history and physical examination at the sixth examination cycle in 1996-1997 and at the ninth examination cycle in 2009 were analyzed. Study participants had a mean age of 57.3 years and were nearly evenly divided between men (48.5%) and women (51.5%). Table 4 shows baseline (1996-1997) statistics regarding hypertensive use and smoking status as well as 12-year follow-up (2008-2009) results regarding the occurrence of incident CHD (coronary death, myocardial infarction, coronary insufficiency, and angina pectoris).

TABLE 4

| Population Statistics | Mean |
| --- | --- |
| % with CHD in 2009 | 6.5% |
| % with hard CHD in 2009 | 3.8% |
| % on hypertensives (baseline) | 21.0% |
| % smokers (baseline) | 14.4% |
| % diabetic (baseline | 7.0% |

Atherotech's VAP technology was used to analyze the serum samples as described herein.

For this study, remnant lipoproteins were defined as VLDL3 and IDL and the cholesterol concentrations, VLD3-C and IDL-C, in each were determined.

The relationship between VLDL3-C, IDL-C and VLDL3-C+IDL-C (total remnants) to 12-year incident CHD was examined using multivariable Cox proportional hazard regression for two models adjusted for Framingham risk factors. Model 1 adjusts for age, sex, systolic blood pressure and use of anti-hypertensives, prevalent diabetes and smoking. Model 2 adjusts for all Model 1 risk factors as well as HDL-C and total cholesterol. Within each model, separate Cox regressions are performed for each lipid variable to determine lipid-specific hazard ratios. CHD related events were adjudicated according to established FCOS procedures.

Figure 4:
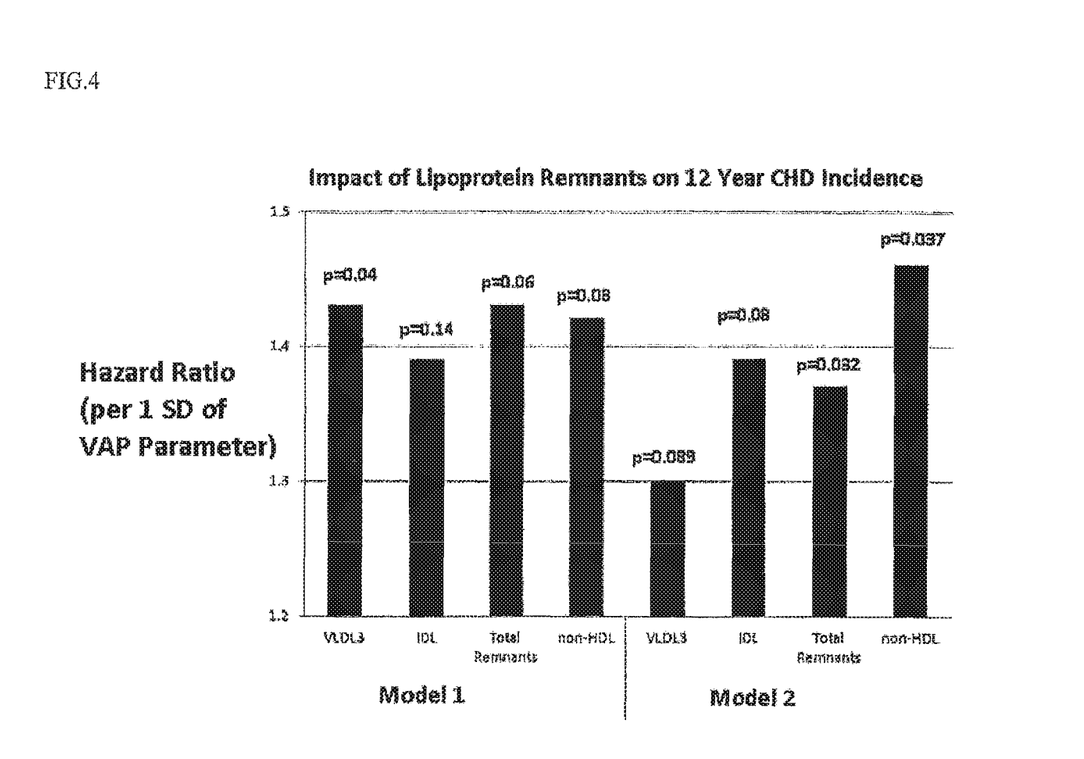
FIG. 4 shows the hazard ratios for various lipoprotein subclasses showing the impact on 12 year coronary heart disease risk in a partially adjusted (model 1, adjusted for age, sex, systolic blood pressure and use of anti-hypertensives, prevalent diabetes and smoking) and model 2 (fully adjusted for adjusted for age, sex, systolic blood pressure and use of anti-hypertensives, prevalent diabetes, smoking, HDL cholesterol and total cholesterol).

The results are shown in FIG. 4. FIG. 4 shows the hazard ratios for a 1 standard deviation increase for selected lipoproteins in both model 1 and model 2. In model 1, VLDL3-C(HR 1.43; 95% CI 1.12-1.82, p<0.004), IDL-C(HR 1.39; 95% CI 1.07-1.80, p<0.014), and total remnants (HR 1.43; 95% CI 1.11-1.85, p<0.032) were all significant predictors of incident CHD. In model 2, VLDL3-C lost significance (HR 1.30; 95% CI 0.96-1.75, p<0.089), but IDL-C(HR 1.39; 955 CI 1.03-1.82, p<0.03) and total remnants (HR 1.37; 95% CI 1.03-1.84, p<0.032) remained significant predictors for incident CUD. Non-HDL-C which broadly includes all atherogenic lipoproteins including remnants was significant in both model 1 (HR 1.42; 95% CI 1.09-1.83, p<0.008) and model 2 (HR 1.46; 95% CI 1.02-2.08, p<0.037).

In this analysis, after controlling for Framingham risk factors in men and women, total remnant lipoprotein cholesterol (cholesterol in IDL and VLDL3) and IDL cholesterol are independent risk factors for incident CHD events over 12 years of follow-up in both model 1 and model 2. While VLDL3 cholesterol was an independent risk factors for incident CHD events in model 1 (adjusted for age, sex, systolic blood pressure and use of anti-hypertensives, prevalent diabetes and smoking), VLDL3 cholesterol lost significance in model 2 (after further adjustment for HDL-C and total cholesterol).

What is claimed:

1. A method for evaluating a subject for treatment for a cardiovascular disease, the method comprising receiving a sample from the subject; subjecting the sample to ultracentrifugation to separate remnant lipoprotein containing IDL lipoprotein and VLDL3 lipoprotein from all other lipoproteins in the sample; determining a cholesterol concentration in the remnant lipoprotein containing IDL lipoprotein and VLDL3 lipoprotein separated from the sample; and initiating treatment for a cardiovascular disease if the cholesterol concentration in the remnant lipoprotein containing IDL lipoprotein and VLDL3 lipoprotein is greater than 30 mg/dl.

2. The method of claim 1, wherein the IDL lipoprotein concentration in the remnant lipoprotein containing IDL lipoprotein and VLDL3 lipoprotein is greater than 20 mg/dl.

3. The method of claim 1, wherein the VLDL3 lipoprotein concentration in the remnant lipoprotein containing IDL lipoprotein and VLDL3 lipoprotein is greater than 10 mg/dl.

4. The method of claim 1, wherein the remnant lipoprotein consists essentially of IDL lipoprotein and VLDL3 lipoprotein.

5. The method of claim 1, wherein the subject is a human.

6. The method of claim 1, wherein the ultracentrifugation is density gradient ultracentrifugation and the density gradient is formed using a bottom layer having a density from 1.15 to 1.25 g/ml and a top layer having a density of 1.0 to 1.10 g/ml.

7. The method of claim 1, wherein the cardiovascular disease is myocardial infarction, coronary heart disease, coronary artery disease, coronary death, coronary insufficiency, angina pectoris or atherosclerosis.

8. The method of claim 1, wherein the subject is an African-American.

9. A method for evaluating a subject for treatment for a cardiovascular disease, the method comprising receiving a sample from the subject; subjecting the sample to ultracentrifugation to separate remnant lipoprotein containing IDL lipoprotein and VLDL3 lipoprotein from all other lipoproteins in the sample; determining a cholesterol concentration in the remnant lipoprotein containing IDL lipoprotein and VLDL3 lipoprotein separated from the sample; and increasing monitoring of the health of the subject, initiating preventive measures in the subject, initiating lifestyle changes in the subject to reduce the risk of cardiovascular disease or a combination of the foregoing if the cholesterol concentration in the remnant lipoprotein containing IDL lipoprotein and VLDL3 lipoprotein is greater than 30 mg/dl.

10. The method of claim 9, wherein the IDL lipoprotein concentration in the remnant lipoprotein containing IDL lipoprotein and VLDL3 lipoprotein is greater than 20 mg/dl.

11. The method of claim 9, wherein the VLDL3 lipoprotein concentration in the remnant lipoprotein containing IDL lipoprotein and VLDL3 lipoprotein is greater than 10 mg/dl.

12. The method of claim 9, wherein the remnant lipoprotein consists essentially of IDL lipoprotein and VLDL3 lipoprotein.

13. The method of claim 9, wherein the subject is a human.

14. The method of claim 9, wherein the ultracentrifugation is density gradient ultracentrifugation and the density gradient is formed using a bottom layer having a density from 1.15 to 1.25 g/ml and a top layer having a density of 1.0 to 1.10 g/ml.

15. The method of claim 9, wherein the cardiovascular disease is myocardial infarction, coronary heart disease, coronary artery disease, coronary death, coronary insufficiency, angina pectoris or atherosclerosis.

16. The method of claim 9, wherein the subject is an African-American.

* * * * *